(12) United States Patent
Becker et al.

(10) Patent No.: US 6,605,693 B1
(45) Date of Patent: Aug. 12, 2003

(54) TRIPTYCENE POLYMERS AND COPOLYMERS

(75) Inventors: Heinrich Becker, Glashütten (DE); Willi Kreuder, Mainz (DE); Josef Salbeck, Kaufungen (DE); Karl Heinz Weinfurtner, Regensburg (DE)

(73) Assignee: Covion Organic Semiconductors GmbH (DE)

( * ) Notice: Subject to any disclaimer, the term of this patent is extended or adjusted under 35 U.S.C. 154(b) by 0 days.

(21) Appl. No.: 09/914,971

(22) PCT Filed: Mar. 9, 1999

(86) PCT No.: PCT/EP99/01505
§ 371 (c)(1),
(2), (4) Date: Feb. 11, 2002

(87) PCT Pub. No.: WO00/53655
PCT Pub. Date: Sep. 14, 2000

(30) Foreign Application Priority Data

Mar. 13, 1998 (DE) .......................................... 198 06 037

(51) Int. Cl.$^7$ ............................................... C08G 75/00
(52) U.S. Cl. ........................ 528/378; 257/40; 428/411.1
(58) Field of Search ................................. 526/242, 243; 257/40; 428/690, 411.1; 528/378

(56) References Cited

U.S. PATENT DOCUMENTS

| 3,242,186 A | * | 3/1966 | Dershowitz |
| 5,247,190 A | * | 9/1993 | Friend et al. ................ 257/103 |
| 5,334,539 A | * | 8/1994 | Shinar et al. .................. 438/22 |
| 5,710,187 A | * | 1/1998 | Steckle et al. ................. 521/64 |
| 5,900,327 A | * | 5/1999 | Pei et al. ..................... 313/504 |

FOREIGN PATENT DOCUMENTS

| DE | 41 21 138 | 1/1993 |
| DE | 197 44 792 | 4/1999 |
| EP | 581 058 | 2/1994 |
| JP | 515 8092 | 6/1993 |
| JP | 5-158092 A | * 6/1993 |

OTHER PUBLICATIONS

Wasielewski et al., "High–Quantum–Yield Long–Lived Charge Separation in a Photosynthetic Reaction Center Model" *J. Am. Chem. Soc.*:107(19):5562–5563 (1985) XP 002092033.

Wasielewski et al., "Ultrafast Photoinduced Electron Transfer in Rigid Donor–Spacer–Acceptor Molecules: Modification of Spacer Energetics as a Probe for Superexchange-"*Tetrahedron*: 45(15):4785–4806 (1989) XP 002092034.

* cited by examiner

*Primary Examiner*—Donald R. Wilson
*Assistant Examiner*—Henry Hu
(74) *Attorney, Agent, or Firm*—Connolly Bove Lodge & Hutz LLP

(57) ABSTRACT

The invention relates to conjugated polymers containing triptycene units. The polymers according to the invention are on the one hand homopolymers comprising a recurring unit containing a triptycenylene radical, and copolymers comprising two or more different recurring units, which may contain a triptycenylene radical or an arylene, heteroarylene, vinylene and ethynylene radical. The polymers according to the invention are employed as electroluminescent materials.

15 Claims, No Drawings

TRIPTYCENE POLYMERS AND COPOLYMERS

The invention relates to conjugated polymers and copolymers containing triptycene moieties.

There is a considerable industrial demand for large-area solid-state light sources for a number of applications, predominantly in the area of display elements, display-screen technology and illumination technology. The requirements made of these light sources cannot at present be met in an entirely satisfactory manner by any of the existing technologies.

As an alternative to conventional display and illumination elements, such as incandescent lamps, gas-discharge lamps and non-self-illuminating liquid-crystal display elements, electroluminescent (EL) materials and devices, such as light-emitting diodes (LEDs), have already been in use for some time.

Besides inorganic electroluminescent materials and devices, low-molecular-weight organic electroluminescent materials and devices have also been known for about 20 years (see, for example, U.S. Pat. No. 3,172,862). Until recently, however, such devices were greatly restricted in their practical usability.

WO 90/13148 and EP-A-0 443 861 describe electroluminescent devices which contain a film of a conjugate polymer as light-emitting layer (semiconductor layer). Such devices offer numerous advantages, such as the possibility of producing large-area, flexible displays simply and inexpensively. In contrast to liquid-crystal displays, electroluminescent displays are self-illuminating and therefore do not require any additional back-lighting source.

A typical device in accordance with WO 90/13148 consists of a light-emitting layer in the form of thin, dense polymer film (semiconductor layer) which comprises at least one conjugated polymer. A first contact layer is in contact with a first surface, a second contact layer is in contact with a further surface of the semiconductor layer. The polymer film of the semiconductor layer has a sufficiently low concentration of extrinsic charge carriers so that, on application of an electric field between the two contact layers, charge carriers are introduced into the semiconductor layer, the first contact layer being positive relative to the other, and the semiconductor layer emitting radiation. The polymers used in such devices are conjugated. The term conjugated polymer is taken to mean a polymer which has a delocalized electron system along the main chain. The delocalized electron system provides the polymer with semiconductor properties and enables it to transport positive and/or negative charge carriers with high mobility.

The polymeric material for the light-emitting layer using WO 90/13148 is poly(p-phenylenevinylene), and it is proposed to replace the phenyl group in a material of this type by a heterocyclic or a fused carbocyclic ring system. In addition, poly(p-phenylene), PPP, is also used as electroluminescent material (G. Grem et al., Synth. Met. 1992, 51, page 383).

Although good results have been achieved with these materials, the color purity, for example, is still unsatisfactory. Furthermore, it is virtually impossible to generate blue or white emission with the polymers disclosed hitherto.

Since, in addition, the development of electroluminescent materials, in particular based on polymers, can in no way be regarded as complete, the producers of illumination and display devices are interested in an extremely wide variety of electroluminescent materials for such devices.

One of the reasons for this is that only the interaction of the electroluminescent materials with the other components of the devices allows conclusions to be drawn on the quality of the electroluminescent material too.

German Patent Application 197 44 792.9, which has an earlier priority date and was published before the priority date of the present application, describes the use of triptycene derivatives as electroluminescent materials. This application relates to the monomeric triptycene derivatives, which, in order to be used as electroluminescent materials, are applied in the form of a film to a substrate by known methods, such as dipping, spin coating, vapor deposition or buffering out under reduced pressure.

The object of the present invention is to provide novel polymeric electroluminescent materials containing triptycene moieties which are suitable, on use in illumination or display devices, for improving the property profile of these devices.

The object has been achieved by a conjugated polymer containing a) from 1 to 100 mol % of at least one recurring unit RU1 of the general formula (I)

—B—Tr—A— (I)

in which Tr is a triptycenylene radical of the general formula (II)

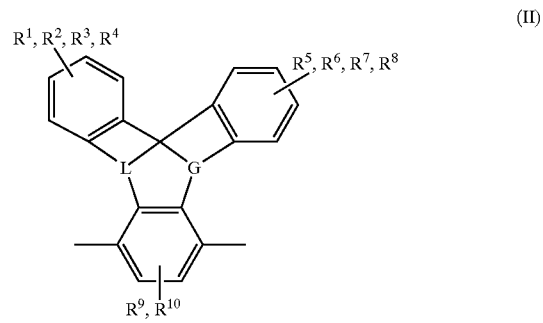

or of the general formula (III)

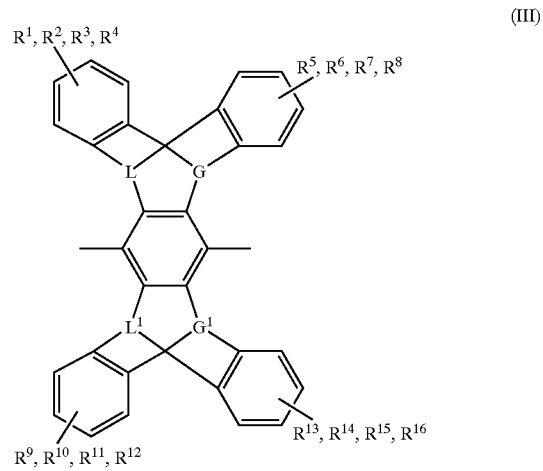

or of the general formula (IV)

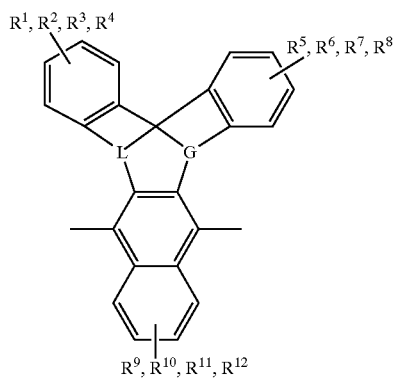

where $R^1$ to $R^{16}$=H, linear or branched $C_1$–$C_{22}$-alkyl or alkoxy, in which one or more non-adjacent $CH_2$ groups may be replaced by —O—, —S—, —CO—, —COO—, —O—CO—, an amino or amide group and in which one or more H atoms may be replaced by F atoms, or $C_6$–$C_{20}$-aryl or aryloxy, COOR, $SO_3$R, CN, halogen or $NO_2$, where G, L and where appropriate $G^1$ and $L^1$=$CR^{17}$, N, P, As, where $R^{17}$=H, $C_1$–$C_{22}$-alkyl or alkoxy, where one or more non-adjacent $CH_2$ groups may be replaced by —O—, —S—, —CO—, —COO—, —O—CO—, an amino or amide group and in which one or more H atoms may be replaced by F atoms, or $C_6$–$C_{20}$-aryl, halogen or CN, A and B are a single bond, a vinylene radical which is optionally substituted by H, linear or branched $C_1$–$C_{22}$-alkyl or alkoxy, in which one or more non-adjacent $CH_2$ groups may be replaced by —O—, —S—, —CO—, —COO—, —O—CO—, an amino or amide group and in which one or more H atoms may be replaced by F atoms, or $C_6$–$C_{20}$-aryl or aryloxy, $C_3$–$C_{20}$-heteroaryl, COOR, $SO_3$R, CN, halogen, $NO_2$, amino, alkylamino or dialkylamino, or are an ethynylene radical, an arylene radical of the general formula (V)

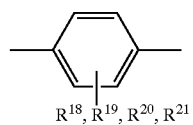

where $R^{18}$ to $R^{21}$ are as defined above for $R_1$ to R16, a heteroarylene radical of the general formula (VI)

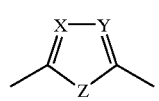

where X and Y=N or $CR^{22}$, and Z=O, S, $NR^{23}$, $CR^{24}R^{25}$, $CR^{26}$=$CR^{27}$ or $CR^{28}$=N—, in which $R^{22}$ to $R^{28}$ are as defined above for $R^1$ to $R^{16}$, or a spirobifluorenylene radical of the general formula (VII)

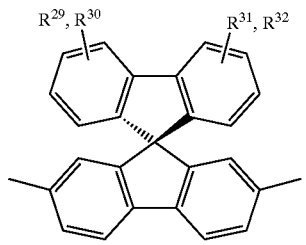

where $R^{29}$ to $R^{32}$ are as defined above for $R^1$ to $R^{16}$, and b) from 0 to 99 mol % of at least one recurring unit RU2 of the general formula (VIII)

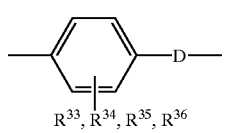

where $R^{33}$ to $R^{36}$ are as defined above for $R^1$ to $R^{16}$, or of the general formula (IX)

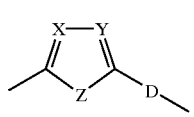

where X, Y and Z are as defined above, and D is a single bond, a vinylene radical which is optionally substituted by H, linear or branched $C_1$–$C_{22}$-alkyl or alkoxy, in which one or more non-adjacent $CH_2$ groups may be replaced by —O—, —S—, —CO—, —COO—, —O—CO—, an amino or amide group and in which one or more H atoms may be replaced by F atoms, or $C_6$–$C_{20}$-aryl or aryloxy, $C_3$–$C_{20}$-heteroaryl, COOR, $SO_3$R, CN, halogen, $NO_2$, amino, alkylamino or dialkylamino, or is an ethynylene radical.

In a preferred embodiment of the invention, L, G and where appropriate $L^1$ and $G^1$ are a CH group.

A and B are a single bond, an optionally substituted vinylene radical, an ethynylene radical, an optionally substituted arylene radical, an optionally substituted heteroarylene radical or a spirobifluorenylene radical.

Preferred substituted vinylene radicals are methylvinylene, phenylvinylene and cyanovinylene.

Particular preference is given to an unsubstituted vinylene radical.

Preferred arylene radicals are 1,4-phenylene, 2,5-tolylene, 1,4-naphthylene, 1,9 antracylene, 2,7-phenantrylene and 2,7-dihydrophenantrylene.

Preferred heteroarylene radicals are 2,5-pyrazinylene, 3,6-pyridazinylene, 2,5-pyridinylene, 2,5-pyrimidinylene, 1,3,4-thiadiazol-2,5-ylene, 1,3-thiazol-2,4-ylene, 1,3-thiazol-2,5-ylene, 2,4-thiophenylene, 2,5-thiophenylene, 1,3-oxazol-2,4-ylene, 1,3-oxazol-2,5-ylene and 1,3,4-oxadiazol-2,5-ylene, 2,5-indenylene and 2,6-indenylene.

Methods for the synthesis of these monomers are based, for example, on the synthesis of 9,9'-spirobifluorene, for example from 2-bromobiphenyl and fluorenone via a Grignard synthesis, as described by R. G. Clarkson, M.

Gomberg, J. Am. Chem. Soc. 1930, 52, page 2881, which is subsequently further substituted in a suitable manner.

Functionalizations of 9,9'-spirobifluorene are described, for example, in J. H. Weisburger, E. K. Weisburger, F. E. Ray, J. Am. Chem. Soc. 1959, 72, 4253; F. K. Sutcliffe, H. M. Shahidi, D. Paterson, J. Soc. Dyers Colour 1978, 94, 306; and G. Haas, V. Prelog, Helv. Chim. Acta 1969, 52, 1202.

The desired substitution pattern of the 9,9'-spirobifluorene monomer is obtained significantly more favorably if the spiro linkage is carried out starting from suitably substituted starting materials, for example with 2,7-difunctionalized fluorenones, and the 2',7'-positions which are still free are then, if desired, further functionalized after build-up of the spiro atom (for example by halogenation or acylation, with subsequent C—C linkage after conversion of the acetyl groups into aldehyde groups, or by build-up of heterocycles after conversion of the acetyl groups into carboxylic acid groups).

The further functionalization can be carried out by methods known from the literature, as described in standard works on organic synthesis, for example Houben-Weyl, Methoden der Organischen Chemie [Methods of Organic Chemistry], Georg-Thieme Verlag, Stuttgart, and in the corresponding volumes of the series "The Chemistry of Heterocyclic Compounds" by A. Weissberger and E. C. Taylor (editors).

The substituted triptycene or heterotriptycene basic structures are accessible by various synthetic routes. At this point, mention may be made by way of example, but not in a restrictive manner, of the following:

1. Syntheses from substituted anthracene (or substituted acridine or substituted phenazine) and decahydroaromatic compounds, for example starting from
   a) substituted o-fluorobromofluorobenzenes with reactive metals, such as, for example, magnesium, for example analogously to G. Wittig, Org. Synth. IV 1963, 964;
   b) substituted o-dihalobenzenes and butyllithium with elimination of metal halide, for example analogously to H. Hart, S. Shamouilian, Y. Takehira J. Org. Chem. 46 (1981) 4427;
   c) substituted monohalobenzenes and strong bases with elimination of hydrogen halide, for example analogously to P. G. Sammes, D. J. Dodsworth, J. C. S. Chem. Commun. 1979, 33.
   d) substituted anthranilic acid derivatives and isoamyl nitrile, for example analogously to C. W. Jefford, R. McCreadie, P. Müller, B. Siegfried, J. Chem. Educ. 48 (1971) 708.
   e) a review of the preparation of a series of substituted dehydroaromatc compounds is given in Houben-Weyl, Methoden der Organischen Chemie [Methods of OrganicChemistry], 4th Edition 1981, Volume V/2b, pp.615, Georg-Thieme-Veriag, Stuttgart.

2. Syntheses by deamination of substituted anthracene-9, 10-imines, for example analogously to L. J. Kricka, J. M. Vemon, J. C. S. Perkin I, 1973, 766.

3. Synthesis by cycloaddition of substituted 1,4-quinones with substituted anthracene derivatives, for example analogously to E. Clar, Chem. Ber. 64 (1931) 1676; W. Theilacker, U. Berger-Brose, K. H. Beyer, Chem. Ber. 93 (1960) 1658; P. D. Bartlett, M. J. Ryan, J. Am. Chem. Soc. 64 (1942) 2649; P. Yates, P. Eaton, J. Am. Chem. Soc. 82 (1960) 4436. V. R. Skvarchenko, V. K. Shalaev, E. I. Klabunovskii, Russ. Chem. Rev. 43 (1974) 951;

Further syntheses of substituted triptycenes are given by way of example in C. F. Wilcox, F. D. Roberts, J. Org. Chem. 30 (1965) 1959; T. H. Regan, J. B. Miller, J. Org. Chem. 32 (1967) 2798.

Further syntheses for heterotrypticenes are given, for example, in D. Hellwinkel et al., Chem. Ber. 111 (1978); or D. Hellwinkel et al., Angew. Chem. 24 (1969) 1049; N. P. McCleland et al., J. Am. Chem. Soc. (1927) 2753; N.A.A. Al-Jabar et al., J. Organomet. Chem. 287 (1985) 57.

Bistryptycene basic structures or heterobistriptycene basic structures are likewise accessible by various synthetic routes. Mention may be made at this point by way of example of the following:

1) Syntheses from substituted anthracene (or substituted acridine or substituted phenazine) and substituted didehydrobenzenes, for example analogously to H. Hart, S. Shamouilian, Y. Takehira J. Org. Chem. 46 (1981) 4427;

2) Synthesis by cycloaddition of substituted anthracene derivatives with 1,4-benzoquinone, for example analogously to E. Clar, Chem. Ber. 64 (1931) 1676; P. Yates, P. Eaton, J. Am. Chem. Soc. 82 (1960) 4436; W. Theilacker, U. Berger-Broske, K. H. Beyer, Chem. Ber. 93 (1960) 1658.

Further syntheses are given by way of example in H. Hart et al., Tetrahedron 42 (1986) 1641; V. R. Skvarchenko et al., Russ. Chem. Rev. 43 (1974) 951; V. R. Skvarchenko et al., J. Org. Chem. USSR (Engl. trans.) 3 (1967) 1477.

In a preferred embodiment, the polymers according to the invention consist of precisely one type of recurring units RU1 (homopolymers). Particular preference is given to homopolymers in which A is selected from the group consisting of 2,5-thiophenylene, 2,5-oxadiazolylene, 1,4-phenylene, vinylene and ethynylene, and B is a single bond.

Preferred homopolymers are furthermore those in which A and B are identical and are selected from the group consisting of 2,5-thiophenylene, 1,4-phenylene, vinylene and ethynylene.

In a further preferred embodiment, the polymers according to the invention comprise from 1 to 99 mol % of recurring units RU2 (copolymers). The copolymers preferably comprise from 5 to 95 mol % of recurring units RU2, particularly preferably from 10 to 90 mol % of recurring units RU2.

Preferred copolymers are furthermore those in which A is a single bond and B is a single bond, a vinylene group or ethynylene group. Particular preference is given to copolymers in which B is a vinylene group.

Preferred copolymers are furthermore binary copolymers comprising recurring units RU1 and recurring units RU2 of the general formula (VIII) or (IX).

Preferred copolymers are furthermore quatemary copolymers comprising recurring units RU1 and two types of recurring units RU2 of the general formula (VIII) or (IX).

Particularly preferred copolymers are those in which the recurring units RU2 are recurring units of the general formula (VIII).

Particular preference is furthermore given to copolymers in which the group D in the general formulae (VIII) and (IX) is a vinylene group.

The polymers are prepared by conventional methods of polymerization reaction, as described, for example, in "Makromoleküle" [Macromolecules] by Hans-Georg Elias (Hüthig & Wepf Verlag Basle-Heidelberg-New York) or in Houben-Weyl, Methoden der organischen Chemie [Methods of Organic Chemistry], Vol. XIV, Makromolekulare Stoffe [Macromolecular Substances] (G. Thieme, Stuttgart, 1961 and 1963). The selection is in each case made depending on the type of functionalization of the monomers and the desired molecular weight.

Starting from the monomers obtained as described, the polymerization to give polymers according to the invention is possible by a plurality of processes.

For example, halogen derivatives of the triptycenes can be polymerized oxidatively (for example using $FeCl_3$, see, inter alia, P. Kovacic et al., Chem. Ber., 87, 1987, 357 to 379; M. Wenda et al., Macromolecules 25, 1992, 5125) or electrochemically (see, inter alia, N. Saito et al., Polym. Bul. 30, 1993, 285).

Polymers according to the invention can likewise be prepared from dihalogen derivatives by polymerization with copper/triphenylphosphine catalysis (see, for example, G. W. Ebert et al., J. Org. Chem. 1988, 53, 4829, or nickel/triphenylphosphine catalysis (see, for example, H. Matsumoto et al., J. Org. Chem. 1983, 48, 840).

Aromatic diboronic acids and aromatic dihalides or aromatic haloboronic acids can be polymerized with palladium catalysis (Suzuki coupling) (see, for example, M. Miyaura et al., Synth. Commun. 11, 1981, 513; R. B. Miller et al., Organometallics 3, 1984, 1261). In a similar manner, aromatic distannanes and aromatic dihalides can be polymerized (see, for example, J. K. Stille, Angew. Chem. Int. Ed. 25,1986, 508).

Furthermore, dibromoaromatic compounds can be converted into dilithio or di-Grignard compounds. These can then be polymerized with further dihaloaromatic compounds by means of $CuCl_2$ (see, for example, G. Wittig et al., Liebigs Ann. Chem. 704, 91,1967; H. A. Stabb et al., Chem. Ber. 100, 1967, 293 and T. Kaufmann, Angew. Chem. 86,1974, 321).

Particular methods are necessary for the preparation of poly(triptycenyl-vinylenes), which are likewise according to the invention. Thus, the synthesis can be carried out, for example, by polycondensation of para-dihalomethyl-substituted triptycene derivatives. The polymerization here is carried out in a suitable solvent by addition of base (see, for example, H.Hörhold et al., Makromol. Chem, Macromol. Symp. 12, 1987, 229–258). Precursor polymerization is likewise possible; in this case, a poly(triptycenylene-vinylene) is prepared by elimination of a precursor radical present (for example $CH_2S^+R_2$) by heat treatment or base treatment (see, for example, R. A. Wessling, J. Polym. Sci; Polym. Sym. 72, 1985, 55–66).

Further ways of preparing poly(triptycenylenes) are, for example, Homer polymerization and Wittig polymerization. In these, two types of monomer (aldehydes with phosphonates (Homer polymerization); aldehydes with triarylalkylphosphonium salts (Wittig polymerization)) are polymerized with addition of a base. In general, these preparation processes are described, for example, in DD 84272, H. Hörhold et al., Makromol. Chem, Macromol. Symp. 12, 1987, 229–258 and H. Horhold et al., Z. Chem. 27, 1987, 126.

Cyano-substituted poly(triptycenylvinylenes) can be prepared by the Knoevenagel reaction. In this, a bis-cyanomethyl-substituted aromatic compound is reacted with a dialdehyde with addition of a base (see, for example, H. Hörhold et al., Plaste und Kautschuk 17, 1970, 84).

For the preparation of copolymers, triptycene or heterotriptycene monomers can be polymerized together with one or more comonomers, as described, for example, in "Makromolekuile" [Macromolecules] by Hans-Georg Elias (Hüthig & Wepf Verlag Basle-Heidelberg-New York), pp. 32–40.

The polymers according to the invention can be worked up by known methods which are familiar to the person skilled in the art, as described, for example, in D. Braun, H. Cherdron, W. Kem, Praktikum der makromolekularen organischen Chemie [Practical Macromolecular Organic Chemistry], 3rd Edn. Hüthig Verlag, Heidelberg, 1979, pp. 87–89 or R. J. Young, P. A. Lovell, Introduction to Polymers, Chapman & Hall, London 1991. For example, the reaction mixture can be filtered, diluted with aqueous acid, extracted and the crude product obtained after drying and stripping-off of the solvent can be further purified by reprecipitation from suitable solvents with addition of precipitants. Polymer-analogous reactions can subsequently be carried out for further functionalization of the polymer. Thus, for example, terminal halogen atoms can be removed reductively by reduction with, for example, $LiAlH_4$ (see, for example, J. March, Advanced Organic Chemistry, 3rd Edn. McGraw-Hill, p. 510).

The polymers according to the invention are suitable for use as electroluminescent materials.

For the purposes of the present invention, the term "electroluminescent materials" is taken to mean materials which can be used as or in an active layer in an electroluminescent device. The term "active layer" means that the layer is capable of emitting light (light-emitting layer) on application of an electric field and/or that it improves the injection and/or transport of the positive and/or negative charges (charge injection or charge transport layer). In addition, the use as electron-blocking layer or hole-blocking layer is a use according to the invention.

The invention therefore also relates to the use of the polymers according to the invention as electroluminescent material. The invention furthermore relates to an electroluminescent material which comprises the polymers according to the invention.

In order to be used as electroluminescent materials, the polymers according to the invention are generally applied in the form of a film to a substrate by known methods familiar to the person skilled in the art, such as dipping, spin coating, vapor deposition or buffering-out under reduced pressure.

The invention likewise relates to an electroluminescent device having one or more active layers, where at least one of these active layers comprises one or more polymers according to the invention. The active layer can be, for example, a light-emitting layer and/or a charge-transport layer and/or a charge-injection layer. The general construction of electroluminescent devices of this type is described, for example, in U.S. Pat. No. 4,539,507 and U.S. Pat. No. 5,151,629.

They usually contain an electroluminescent layer between a negative electrode and a positive electrode, where at least one of the electrodes is transparent for part of the visible spectrum. In addition, one or more electron-injection and/or electron-transport layers can be introduced between the electroluminescent layer and the negative electrode and/or one or more hole-injection and/or hole-transport layers can be introduced between the electroluminescent layer and the positive electrode. Suitable negative electrodes are preferably metals or metal alloys, for example Ca, Mg, Al, In or Mg/Ag. The positive electrodes can be metals, for example Au, or other metallically conducting substances, such as oxides, for example ITO (indium oxide/tin oxide) on a transparent substrate, for example made of glass or a transparent polymer.

In operation, the negative electrode is set to a negative potential compared with the positive electrode. Electrons are injected by the negative electrode into the electron-injection layer/electron-transport layer or directly into the light-emitting layer. At the same time, holes are injected by the positive electrode into the hole-injection layer/hole-transport layer or directly into the light-emitting layer.

The injected charge carriers move through the active layers toward one another under the effect of the applied voltage. This results in electron/hole pairs recombining at the interface between the charge-transport layer and the light-emitting layer or within the light-emitting layer with emission of light. The color of the emitted light can be varied by means of the materials used as light-emitting layer.

Electroluminescent devices are used, for example, as self-illuminating display elements, such as control lamps, alphanumeric displays, signs and in opto-electronic couplers.

Compounds of the formula (I) are furthermore suitable, for example, for use in optical storage media, as photorefractive materials, for nonlinear-optical (NLO) applications, as optical brighteners and radiation converters and, preferably, as hole-transport materials in photovoltaic cells, as described, for example, in WO-A 97/10 617 and DE-A 197 11 713, to which reference is made for these applications.

The polymers according to the invention have excellent solubility in organic solvents. The film-forming properties are excellent compared with poly(p-phenylene). Particular emphasis should be placed on the temperature stability of the emission color, i.e. the fact that the morphology of the polymer is not destroyed with thermal activation. Furthermore, high charge carrier mobilities are observed.

The invention is explained in greater detail by the examples below without being restricted thereby.

EXAMPLES

Polymer LEDs were produced by the general process outlined below. Naturally, this had to be adapted to the particular circumstances (for example polymer viscosity and optimum layer thickness of the polymer in the device and the like) in individual cases. The LEDs described below were in each case one-layer systems, i.e. substrate1//ITO//polymer1//negative electrode.

General process for the production of high-efficiency long-life LEDs using triptycene-containing polymers:

After the ITO-coated substrates (for example glass support, PET foil) had been cut to the correct size, they were cleaned in a number of cleaning steps in an ultrasound bath (for example, soap solution, Millipore water, isopropanol). For drying, they were blown with an $N_2$ gun and stored in a desiccator. Before coating with the polymer, they were treated with an ozone plasma unit for about 20 minutes. A solution of the respective polymer (in general with a concentration of 4–25 mg/ml in, for example, toluene, chlorobenzene, xylene:cyclohexanone (4:1)) was prepared and dissolved by stirring at room temperature. Depending on the polymer, it may also be advantageous to stir the solution at 50–70° C. for some time. When the polymer had dissolved completely, it was filtered through a 5 gm filter and coated on at variable speeds (400–6000 r.p.m.) using a spin coater. It was possible to vary the layer thicknesses thereby in the range from about 50 to 300 nm. Electrodes were subsequently applied to the polymer films. This was generally carried out by thermal evaporation (Balzer BA360 or Pfeiffer PL S 500). The transparent ITO electrode was then connected as positive electrode and the metal electrode (for example Ca) as negative electrode, and the device parameters were determined.

Example M1

Synthesis of Dihydrotriptycene-1,4-quinone 17.8 g (100 mmol) of anthracene and 10.8 g (100 mmol) of p-benzoquinone (freshly sublimed) were dissolved in 200 ml of p-xylene at 135° C. under nitrogen. After a few minutes, the red-colored solution began to deposit a yellow, crystalline precipitate. After 4 hours, the mixture was allowed to cool to room temperature, and the precipitate was filtered off with suction. The yellow solid was rinsed with p-xylene and dried under reduced pressure. The resultant 26.0 g (91 mmol, 91% yield) were heated to 130° C. in 100 ml of p-xylene under $N_2$, and this temperature was maintained for 0.5 hour, the mixture was cooled to room temperature, and the product was filtered off with suction, rinsed with methanol and dried, giving 23.5 g (82 mmol, 82% yield) of dihydrotriptycene-1,4-quinone as pale yellow crystals.

Melting point: 232° C.

$^1$H NMR: (400 MHz; $CDCl_3$): [ppm]=3.15 (t, 2H, tert. H), 4.86 (s, 2H, enyl H), 6.30 (s, 2H, bridgehead H) 7.07 and 7.39 (4H, m, J=5.3 Hz, 2.3 Hz-phenyl H), 7.17–7.20 ppm, m, 4H, phenyl H).

Example M2

Synthesis of 1,4-Triptycene-1,4-quinone 37.0 g (129 mmol) of dihydrotriptycene-1.4-qione were suspended in 350 ml of glacial acetic acid, and 1.5 ml of HBr (48% strength in water) were added at the boil. The mixture was refluxed for 2 hours. A solution of 13.0 g of $KIO_3$ (60 mmol) was then added dropwise at the boil over the course of 5 minutes. A yellow coloration of the suspension was immediately evident. The mixture was allowed to cool, 200 ml of water were added at 50° C., and the solid was filtered off with suction, then washed a number of times with $Na_2SO_3$ solution and subsequently a number of times with water and dried under reduced pressure. The crude product (35.2 g, 96% yield) was triturated twice for one hour each time in 150 ml of isopropanol, giving 30.9 g (108.7 mmol, 84% yield) of 1,4-triptycene-1,4-quinone as a luminescent-yellow powdery substance.

Melting point: 273–275° C. $^1$H NMR: (400 MHz; $CDCl_3$): [ppm]=5.79 (s, 2H, bridgehead H), 6.59 (s, 2H, enyl H), 7.03 and 7.42 (m, 8H, J=2.3 Hz, 5.3 Hz, AB system phenyl H).

Example M3

Synthesis of 1,4-Dihydroxy-1,4-dimethyltriptycene 148 ml (237 mmol, 2.7 eq) of a 1.6 M solution of methyllithium in diethyl ether were introduced into a 1 l four-necked flask together with 300 ml of THF (distilled from Na/benzophenone) and cooled to −78° C. (acetone/dry ice). At the same time, a solution of 25.0 g (87.9 mmol) of 1,4-triptycene-1,4-quinone in 600 ml of THF was cooled to the same temperature. The solution of 1,4-triptycene-1,4-quinone was transferred into a dropping funnel, which was additionally cooled by means of dry ice. The starting-material solution was slowly added dropwise (1 hour) with vigorous stirring, the solution immediately changing color from blue to blue-green. When the addition was complete, the temperature was maintained for a further hour, and the cooling was subsequently removed. The mixture was allowed to warm to room temperature and was stirred overnight. The suspension was evaporated to about 200 ml under reduced pressure and subsequently poured into a mixture of 1.4 L of ice-water on 10 g of $NH_4Cl$. During the pouring-in, heat was evolved and a pale beige precipitate deposited, which liquified on warming to room temperature. The resultant oil was separated off, and the water phase was extracted three times with 500 ml of $CH_2Cl_2$. The combined organic phases were washed twice with 200 ml of water each time, dried using $Na_2SO_4$ and evaporated as far as possible on a rotary evaporator.

A brown, viscous material remained which was treated with 30 ml of diethyl ether/hexane 2:1 in an ultrasound bath until all the oil had dissolved and a white precipitate had formed. The precipitate was filtered off with suction, and the mother liquor was again evaporated in a rotary evaporator and treated in the same way, the volumes of $Et_2O$/hexane mixture being chosen somewhat smaller each time. The operation was repeated until no further precipitate deposited. For further purification, the reaction mixture was refluxed in diethyl ether, cooled to 20° C. and filtered off with suction, giving 14.9 g (47.1 mmol, 54%) of 1,4-dihydroxy-1,4-dimethyltriptycene as a white powder.

$^1$H NMR: (400 MHz; DMSO-$d_6$):=1.09 (s, 6H, methyl H); 4.84 (s, 2H, hydroxy H); 5.34 (s, 2H, quinone H); 5.63 (s, 2H, bridgehead H); 6.90, 6.92, 7.28, 7.33 (m, each 2H, J=5.3 Hz and 2.3 Hz, phenyl H). $^1$H NMR: (400 MHz; $CDCl_3$):= 1.27 (s, 6H, methyl H); 1.63 (s, 2H, hydroxy H); 5.39 (s, 2H, quinone H); 5.54 (s, 2H, bridgehead H); 6.91 (m, 2H, J=5.5 Hz and 2.3 Hz, phenyl H); 6.95 m, 2H, J=5.3 Hz and 2.0 Hz, phenyl H); 7.32 (m, 4H, J=5.3 Hz, 2.3 Hz and 2.0 Hz, phenyl H).

Example M4

Synthesis of 1.4-Dimethyltriptycene 6.70 g (53.3 mmol, 2.1 eq) of $SnCl_2.2 H_2O$ were dissolved in 200 ml of 50% strength acetic acid. A methanolic solution of 8.44 g (25.7 mmol) of 1,4-dihydroxy-1,4-dimethyltriptycene was slowly added dropwise thereto at such a rate that the temperature did not rise higher than a maximum of 45° C. The reaction solution adopted a yellowish coloration, and a white precipitate deposited. When the addition was complete, the mixture was stirred at room temperature for a further 2 hours and then cooled to –18° C., and the resultant precipitate was filtered off with suction, washed with about 1 L of water until acid-free and dried under reduced pressure. The resultant mother liquor was then evaporated somewhat in a rotary evaporator, and the precipitate which deposited on re-cooling was again filtered off with suction, giving 7.0 g of crude product. The compound was dissolved in about 300 ml of acetone at the boil and subsequently precipitated with 50 ml of water. The solution was cooled in the ice compartment, and the precipitate was filtered off with suction. Repetition of the procedure gave 5.20 g (18.4 mmol, 72%) of 1,4-dimethyltriptycene as white sparkling crystals.

Melting point: 246–249° C. $^1$H NMR: (400 MHz; DMSO-$d_6$):=2.43 (s, 6H, methyl H); 5.80 (s, 2H, bridgehead H); 6.71 (s, 2H, phenyl H); 6.98 and 7.45 (m, 8H, J=2.3 Hz, 5.3 Hz, AB system, phenyl H). $^1$H NMR: (400 MHz; $CDCl_3$) :=2.46 (s, 6H, methyl H); 5.64 (s, 2H, bridgehead H); 6.70 (s, 2H, phenyl H); 6.97 and 7.36 (m, 8H, J=2.3 Hz, 5.3 Hz, AB system, phenyl H).

Example M5

Synthesis of 1,4-bis(Bromomethyl)triptycene 5.20 g (18.4 mmol) of 1,4-dimethyltriptycene were dissolved in 150 ml of dry tetrachloromethane, and 3.45 g (19.3 mmol) of N-bromosuccinimide and 0.20 g (1.22 mmol) of diazoisobutyronitrile were added. The suspension was heated under a gentle reflux with irradiation with light. The mixture was allowed to react for one hour. After checking by TLC (hexane/$CH_2Cl_2$1:1), N-bromosuccinimide was added until the spot between the starting material and product had disappeared. The mixture was then allowed to cool, and the succinimide was separated off by filtration. The reaction solution was evaporated as far as possible (30 ml) in a rotary evaporator, a little hexane was added, and the mixture was cooled. The precipitate was filtered off with suction and dried, giving 7.70 g (17.5 mmol, 95%) of pale-yellow crude product. For purification, the product was recrystallized from glacial acetic acid, giving 5.6 g (12.7 mmol, 70%) of 1,4-bis(bromomethyl)triptycene as colorless crystals.

Melting point: 198–208° C. $^1$H NMR: (400 MHz; $CDCl_3$) :=4.67 (s, 4H, bromomethyl H); 5.40 (s, 2H, bridgehead H), 6.90 (s, 2H, phenyl H); 7.02 and 7.47 (m, J=5.3 Hz, 3.3 Hz, 8H, AB system, phenyl H).

Example P1

Copolymer of 80% of 2,5-bis(Chloromethyl)-1-methoxy-4-(3,7-dimethyloctyloxy)benzene and 20% of 1,4-bis(Bromomethyl)triptycene (Polymer 1)

720 ml of dry and $O_2$-free 1,4-dioxane were heated to 95° C. in a dry 2 L four-necked flask fitted with mechanical Teflon stirrer, reflux condenser, thermometer and dropping funnel. A solution 2.89 g (8 mmol) of 2,5-bis (chloromethyly-1-methoxy-4-(3',7'-dimethyloctyloxy) benzene and 880 mg (2 mmol) of 1,4-bis(bromomethyl) triptycene in 10 ml of dry 1,4-dioxane were then added. A solution of 2.92 g (26 mmol) of potassium tert-butoxide in 25 ml of dry 1,4-dioxane was then added dropwise to the vigorously stirred mixture over the course of 5 minutes. During this operation, the color changed from colorless via yellow to orange-red. After 5 minutes, a further 2.24 g (20.0 mmol) of potassium tert-butoxide, dissolved in 20 ml of 1,4-dioxane, were added. After the mixture had been stirred at 95–97° C. for 2 hours, it was cooled to 55° C., and a mixture of 4 ml of acetic acid and 4 ml of 1,4-dioxane was added. The solution, which was now orange, was poured into 1 L of vigorously stirred water. The precipitated polymer was isolated by filtration through a polypropylene filter and dried under reduced pressure. The crude yield was 2.50 g (8.7 mmol, 87%).

The polymer was dissolved in 330 ml of THF with heating to 60° C. and precipitated by addition of 330 ml of methanol at 40° C. After drying under reduced pressure, this step was repeated. Drying under reduced pressure gave 1.46 g (=5.10 mmol, 51%) of polymer 1 as pale-orange fibers.

The content of triptycene groups was determined by $^1$H-NMR spectroscopy. To this end, the signal of the triptycene bridgehead H atoms (6.0 ppm) was integrated and compared with the $OCH_3$ and $OCH_2$ signals at 4.2–3.6 ppm; 9% of triptycene units were determined in the polymer.

$^1$H-NMR (400 MHz, $CDCb_3$): (ppm)=7.9–6.6 (broad multiplet, 5.6 H; aryl H, olefin H); 6.0 (broad singlet; 0.4H; triptycene bridgehead H); 4.2–3.6 (br. m [?], 4H; $OCH_2$, $OCH_3$); 2.0–0.9 (broad multiplet, 9.6H; aliphatic side chain); 0.89, 0.86 (2 singlets, 7.2H; 3×$CH_3$). GPC: THF+ 0.25% oxalic acid; column set SDV500, SDV1000, SDV10000 (PSS), 35° C., UV detection 254 nm, polystyrene standard: $M_w$=3.0 $10^5$ g/mol, $M_n$=4.5 $10^4$ g/mol.

Electroluminescence measurement: 0.34% maximum quantum efficiency at 5.2 V, a luminance of 100 cd/ml was achieved at 6.81 V, 15.07 mA/cm$^2$.

Example P2

Copolymer of 91% of 2,5-bis(Chloromethyl)-1-methoxy-4-(3,7-dimethyloctyloxy)benzene and 9% of 1,4-bis(Bromomethyl)triptycene (Polymer 2)

1000 ml of dry and $O_2$-free 1,4-dioxane were heated to 88–90° C. in a dry 2 L four-necked flask fitted with precision-glass stirrer, reflux condenser, thermometer and dropping funnel. A solution 4.34 g (12 mmol) of 2,5-bis (chloromethyl)-1-methoxy-4-(3',7'-dimethyloctyloxy) benzene and 528 mg (1.2 mmol) of 1,4-bis(bromomethyl)-triptycene in 20 ml of dry 1,4-dioxane were then added. A solution of 3.85 9 (34.3 mmol) of potassium tert-butoxide in 34 ml of dry 1,4-dioxane was then added dropwise to the reaction mixture over the course of 5 minutes with vigorous stirring. During this operation, the color changed from colorless via yellow to orange-red. After 5 minutes, a further 3.85 g (34.3 mmol) of potassium tert-butoxide, dissolved in 26 ml of 1,4-dioxane, were added. After the mixture had been stirred at 88° C. for 2 hours, it was cooled to 55° C., and 12 ml of a 1,4-dioxane/glacial acetic acid 1:1 mixture were added. The viscous solution, which was now orange, was poured into 1 L of vigorously stirred water. The precipitated polymer was isolated by filtration through a polypropylene filter and dried under reduced pressure. 3.4 g of crude polymer were obtained.

The polymer was dissolved in 450 ml of THF with heating to 60° C. and precipitated by addition of 560 ml of methanol at a temperature of <40° C. After drying under reduced pressure, this step was repeated. Drying under reduced pressure gave 2.60 g (=9.03 mmol, 68%) of polymer 2 as pale-orange fibers. The content of triptycene groups was determined by $^1$H-NMR spectroscopy. To this end, the signal of the triptycene bridgehead H (6.0 ppm) was integrated and compared with the OCH$_3$ and OCH$_2$ signals at 4.2–3.6 ppm; 3.5% of triptycene units were determined in the polymer.

$^1$H-NMR (400 MHz, CDCl$_3$): (ppm)=7.9–6.6 (broad multiplet, 4H; aryl H, olefin H); 6.0 (broad singlet; add. 0.02H; triptycene bridgehead H); 4.2–3.6 (br. m, 5H; OCH$_2$, OCH$_3$); 2.0–0.9 (broad multiplet, 10H; aliphatic side chain); 0.89, 0.86 (2 singlets, 9H; 3×CH$_3$). GPC: THF+0.25% oxalic acid; column set SDV500, SDV1000, SDV10000 (PSS), 35° C., UV detection 254 nm, polystyrene standard: M$_w$=2.0 10$^5$ g/mol, M$_n$=3.1 10$^4$ g/mol.

Electroluminescence measurement: 0.21% maximum quantum efficiency at 5.2 V, a luminance of 100 cd/m$^2$ was achieved at 5.05 V, 11.17 mA/cm$^2$.

Copolymer of 80% of 2,5-bis(chloromethyl)3'-(3,7-dimethyloctyloxy)biphenyl and 20% of 1,4-bis (bromomethyl)triptycene (polymer 3):

0.72 kg of dry and O$_2$-free 1,4-dioxane were introduced into a dry 2 L four-necked flask fitted with mechanical stirrer, reflux condenser, thermometer and dropping funnel and heated to 98° C. with stirring. A solution of 3.26 g (8 mmol) of 2,5-bis(chloromethyl)-3'(3,7-dimethyloctyloxy) biphenyl and 0.88 g (2 mmol) of 1,4-bis(bromomethyl) triptycene, dissolved in 30 ml of dry 1,4-dioxane, was then added. A solution of 2.87 g (26 mmol, 2.6 equivalents) of potassium tert-butoxide in 26 ml of dry 1,4-dioxane was then added dropwise to the vigorously stirred mixture over the course of 5 minutes. During this operation, the color changed from colorless via green to pale orange; the viscosity of the solution increased slightly. After the mixture had been stirred at 98° C. for 5 minutes, a further 2.24 g (20 mmol, 2.0 equivalents) of potassium tert-butoxide in 20 ml of 1,4-dioxane were added over the course of one minute. After the mixture had been stirred at 95–98° C. for a further 2 hours, it was cooled to 50° C., and a mixture of 4 ml of acetic acid and 4 ml of 1,4-dioxane was added. After the mixture had been stirred for a further 20 minutes, the polymer was precipitated by addition of the reaction solution to 0.7 L of vigorously stirred water. The resultant polymer was filtered off and washed twice with 100 ml of methanol each time. Drying at room temperature under reduced pressure gave 3.17 g (9.8 mmol, 98%) of crude polymer 3.

The crude product was dissolved in 400 ml of THF with heating to 60° C. and precipitated by addition of 400 ml of methanol. After the product had been dried under reduced pressure and washed with 100 ml of methanol, this step was repeated. Drying for 2 days under reduced pressure gave 1.84 g (=5.7 mmol, 57%) of polymer 3 as pale-orange fibers.

The content of triptycene groups was determined by $^1$H-NMR spectroscopy. To this end, the signal of the triptycene bridgehead H (5.9 ppm) was integrated and compared with the OCH$_2$ signal at 4.0 ppm; 14% of triptycene units were present in the polymer.

$^1$H-NMR (400 MHz, CDCl$_3$): (ppm)=7.9–6.1 (broad multiplet, 9.2H; aryl and olefin H); 5.9 (broad singlet; 0.28H; triptycene bridgehead H); 4.0 (broad singlet, 1.6H); 1.95–0.85 (broad multiplet, 15.2H; aliphatic H). GPC: THF+0.25% oxalic acid; column set SDV500, SDV1000, SDV10000 (PSS), 35° C., UV-detection 254 nm, polystyrene standard: M$_w$=4.4 10$^5$ g/mol, M$_n$=9.1 10$^4$ g/mol.

Electroluminescence measurement: 0.47% maximum quantum efficiency at 10.7 V, a luminance of 100 cd/M$^2$ was achieved at 10.9 V$_{max}$=517 nm.

Example P4

Copolymer of 75% of 2,5-bis(Chloromethyl-1-methoxy-4-(3,7-dimethyloctyloxy)benzene and 25% of 1,4-bis(Bromomethyl)triptycene (polymer 4)

385 ml of dry and O$_2$-THF were introduced into a dry 500 ml four-necked flask fitted with mechanical Teflon stirrer, reflux condenser, thermometer and dropping funnel. 1.58 g (3.6 mmol) of 2,5-bis(bromomethyl)-1-methoxy4-(3',7'-dimethyloctyloxy)benzene and 528 mg of (1.2 mmol) of 1,4-bis(bromomethyl)triptycene were then added. A solution of 1.32 g (11.8 mmol) of potassium tert-butoxide in 12 ml of dry THF was then added dropwise to the vigorously stirred mixture over the course of 5 minutes. During this operation, the color changed from colorless via yellow to orange-red. After 5 minutes, a further 1.1 g (9.8 mmol) of potassium tert-butoxide, dissolved in 10 ml of THF, were added in one portion. After the mixture had been stirred at room temperature for 2 hours, it was heated at 60° C. for one hour, and a mixture of 2 ml of acetic acid and 2 ml of 1,4-dioxane was added. The solution, which was now orange, was poured into 1 L of vigorously stirred water. The precipitated polymer was isolated by filtration through a polypropylene filter and dried under reduced pressure. The crude yield was 1.2 g. The polymer was dissolved in 160 ml of THF with heating to 60° C. and precipitated by addition of 200 ml of methanol at room temperature. After drying under reduced pressure, this step was repeated. Drying under reduced pressure gave 0.89 g (=2.98 mmol, 62%) of polymer 4 as pale-orange fibers.

The content of triptycene groups was determined by $^1$H-NMR spectroscopy. To this end, the signal of the triptycene bridgehead H (6.0 ppm) was integrated and compared with the OCH$_3$ and OCH$_2$ signals at 4.2–3.6 ppm; 15% of triptycene units were determined in the polymer.

$^1$H-NMR (400 MHz, CDCl$_3$): (ppm)=7.9–6.6 (broad multiplet, 4H; aryl H, olefin H); 6.0 (broad singlet; 0.3 additional H; triptycene bridgehead H); 4.2–3.6 (broad multiplet, 5H); OCH$_2$, OCH$_3$); 2.0–0.9 (broad multiplet, 10H; aliphatic side chain); 0.89, 0.86 (2 singlets, 9H; 3×CH$_3$). GPC: THF+0.25% oxalic acid; column set SDV500, SDV1000, SDV10000 (PSS), 35° C., UV detection 254 nm, polystyrene standard: $M_w=3.0\ 10^5$ g/mol, $M_n=4.5\ 10^4$ g/mol. Electroluminescence measurement: 0.96% maximum quantum efficiency at 6.01 V, a luminance of 100 cd/m² was achieved at 4.11 V/1 6.07 mA/cm².

What is claimed is:

1. A conjugated polymer comprising a) from 1 to 100 mol % of at least one recurring unit RU1 of the formula (I)

—B—Tr—A— (I)

in which Tr is a triptycenylene radical of the formula (II)

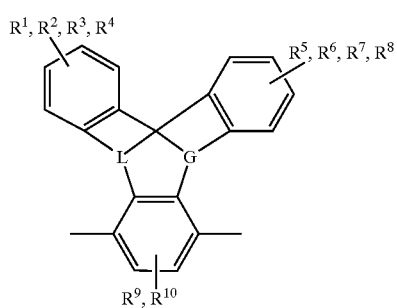

(II)

or of the formula (III)

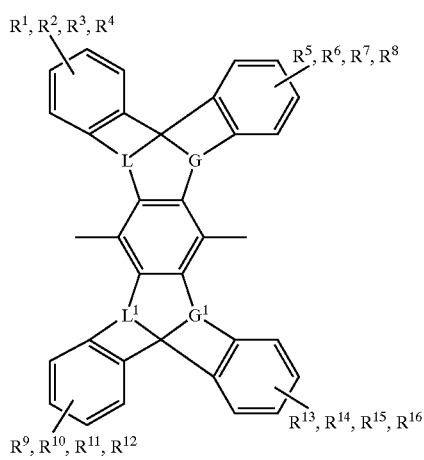

(III)

or of the formula (IV)

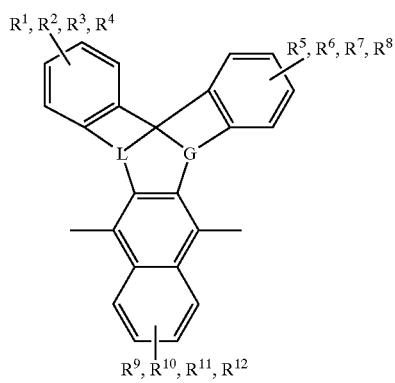

(IV)

wherein $R^1$ to $R^{16}$ are identical or different and are H;

linear or branched $C_1$–$C_{22}$-alkyl in which one or more non-adjacent $CH_2$ groups are optionally replaced by —O—, —S—, —CO—, —COO—, —O—CO—, an amino or amide group and in which one or more H atoms are optionally replaced by F atoms;

linear or branched $C_1$–$C_{22}$-alkoxy, in which one or more non-adjacent $CH_2$ groups are optionally replaced by —O—, —S—, —CO—, —COO—, —O—CO—, an amino or amide group and in which one or more H atoms are optionally replaced by F atoms, $C_6$–$C_{20}$-aryl, $C_6$–$C_{20}$-aryloxy,

COOR, $SO_3R$,

CN, halogen or $NO_2$,

G, L, and where appropriate $G^1$ and $L^1$ are identical or different and are $CR^{17}$, N, P or As and $R^{17}$ is H, $C_1$–$C_{22}$-alkyl in which one or more non-adjacent $CH_2$ groups are optionally replaced by —O—, —S—, —CO—, —COO—, —O—CO—, an amino or amide group and in which one or more H atoms are optionally replaced by F atoms, $C_1$–$C_{22}$-alkoxy, in which one or more non-adjacent $CH_2$ groups are optionally replaced by —O—, —S—, —CO—, —COO—, —O—CO—, an amino or amide group and in which one or more H atoms are optionally replaced by F atoms, $C_6$–$C_{20}$-aryl, halogen or

CN,

A and B are identical or different and are a single bond, a vinylene radical which is optionally substituted by H, linear or branched $C_1$–$C_{22}$-alkyl in which one or more non-adjacent $CH_2$ groups is optionally replaced by —O—, —S—, —CO—, —COO—, —O—CO—, an amino or amide group and in which one or more H atoms are optionally replaced by F atoms, linear or branched $C_1$–$C_{22}$-alkoxy, in which one or more non-adjacent $CH_2$ groups is optionally replaced by —O—, —S—, —CO—, —COO—, —O—CO—, an amino or amide group and in which one or more H atoms are optionally replaced by F atoms, or $C_6$–$C_{20}$-aryl, $C_6$–$C_{20}$-aryloxy, $C_3$–$C_{20}$-heteroaryl,

COOR, $SO_3R$,

CN, halogen, $NO_2$, amino, alkylamino, dialkylamino, an ethynylene radical, an arylene radical of the formula V

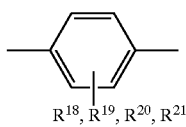
(V)

where $R^{18}$ to $R^{21}$ are identical or different and are as defined above for $R^1$ to $R^{16}$, a heteroarylene radical of the formula (VI)

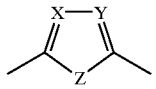
(VI)

X and Y are identical or different and are N or $CR^{22}$, and

Z is O, S, $NR^{23}$, $CR^{24}R^{25}$, $CR^{26}=CR^{27}$ or $CR^{28}=N—$, in which $R^{22}$ to $R^{28}$ are or different and are as defined above for $R^1$ to $R^{16}$, or a spirobifluorenylene radical of the formula (VII)

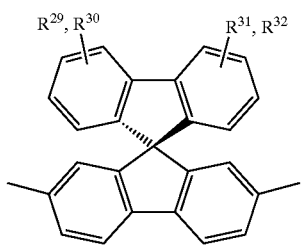
(VII)

where $R^{29}$ to $R^{32}$ are identical or different and are defined above for $R^1$ to $R^{16}$, and b) from 0 to 99 mol % of at least one recurring unit RU2 of the formula (VIII)

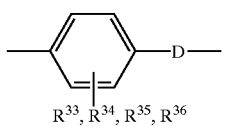
(VIII)

where $R^{33}$ to $R^{36}$ are identical or different and are defined above for $R^1$ to $R^{16}$, or of the formula (IX)

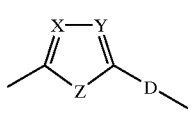
(IX)

where X, Y and Z are as defined above, and

D is a single bond, a vinylene radical which is optionally substituted by H, linear or branched $C_1$–$C_{22}$-alkyl in which one or more non-adjacent $CH_2$ groups are optionally replaced by —O—, —S—, —CO—, —COO—, —O—CO—, an amino or amide group and in which one or more H atoms are optionally replaced by F atoms, linear or branched $C_1$–$C_{22}$-alkoxy, in which one or more non-adjacent $CH_2$ groups are optionally replaced by —O—, —S—, —CO—, —COO—, —O—CO—, an amino or amide group and in which one or more H atoms are optionally replaced by F atoms, $C_6$–$C_{20}$-aryl $C_6$–$C_{20}$-aryloxy, $C_3$–$C_{20}$-heteroaryl,

COOR, $SO_3R$,

CN, halogen, $NO_2$, amino, alkylamino, dialkylamino, or an ethynylene radical.

2. The polymer as claimed in claim 1, in which L and G and optionally $L^1$ and $G^1$ are a CH group.

3. The polymer as claimed in claim 1, which is a homopolymer comprising recurring units RU1.

4. The polymer according to claim 3, wherein A is selected from the group consisting of 2,5-thiophenylene, 2,5-oxadiazolylene, 1,4-phenylene, vinylene and ethynylene, and B is a single bond.

5. The polymer according to claim 3, wherein A and B are identical and are selected from the group consisting of 2,5-thiophenylene, 1,4-phenylene, vinylene and ethynylene.

6. The polymer according to claim 1, comprising from 1 to 99 mol % of recurring units RU2.

7. The polymer according to claim 6, wherein A is a single bond and B is a single bond, a vinylene group or an ethynylene group.

8. The polymer according to claim 7, wherein B is a vinylene group.

9. The polymer according to claim 6, wherein the polymer is a binary copolymer comprising recurring units RU1 and recurring units RU2 of the formula (VIII) or (IX).

10. The polymer according to claim 6, which the polymer is a ternary copolymer comprising recurring units RU1 and two types of recurring units RU2 of the formula (VIII) or (IX).

11. The polymer according to claim 10, wherein the recurring units RU2 are recurring units of the formula (VIII).

12. The polymer according to claim 10, wherein D is a vinylene group.

13. An electroluminescent material comprising the polymer as claimed in claim 1.

14. A process for the preparation of an electroluminescent material which comprises applying the polymer as claimed in claim 1 in the form of a film to a substrate.

15. An electroluminescent device which comprises one or more active layers, where at least one of these active layers comprises the polymer as claimed in claim 1.

* * * * *

UNITED STATES PATENT AND TRADEMARK OFFICE
CERTIFICATE OF CORRECTION

PATENT NO.    : 6,605,693 B1
DATED         : August 12, 2003
INVENTOR(S)   : Heinrich Becker et al.

It is certified that error appears in the above-identified patent and that said Letters Patent is hereby corrected as shown below:

<u>Column 17,</u>
Line 22, "are or different" should read -- are identical or different --.

Signed and Sealed this

Sixth Day of April, 2004

JON W. DUDAS
*Acting Director of the United States Patent and Trademark Office*